US012558560B2

(12) United States Patent
Jordan

(10) Patent No.: US 12,558,560 B2
(45) Date of Patent: Feb. 24, 2026

(54) SYSTEMS AND METHODS FOR IMPROVING DELIVERY OF THERAPEUTICS TO THE SPINAL CORD

(71) Applicant: SYNAPTEC NETWORK, INC., Santa Monica, CA (US)

(72) Inventor: Sheldon Jordan, Pacific Palisades, CA (US)

(73) Assignee: Synaptec Network, Inc., Santa Monica, CA (US)

( * ) Notice: Subject to any disclaimer, the term of this patent is extended or adjusted under 35 U.S.C. 154(b) by 393 days.

(21) Appl. No.: 16/867,085

(22) Filed: May 5, 2020

(65) Prior Publication Data

US 2020/0353272 A1     Nov. 12, 2020

Related U.S. Application Data

(60) Provisional application No. 62/843,663, filed on May 6, 2019.

(51) Int. Cl.
*A61N 2/00*          (2006.01)
*A61F 7/02*          (2006.01)
(Continued)

(52) U.S. Cl.
CPC ................ *A61N 2/002* (2013.01); *A61F 7/02* (2013.01); *A61N 1/36062* (2017.08); *A61N 2/006* (2013.01); *A61N 2/02* (2013.01); *A61N 5/0622* (2013.01); *A61N 7/00* (2013.01); *A61N 2005/0659* (2013.01); *A61N 2007/0026* (2013.01)

(58) Field of Classification Search
CPC ................ A61N 2/002; A61N 1/36062; A61N 1/05551; A61N 2/006; A61N 2007/0026
See application file for complete search history.

(56) References Cited

U.S. PATENT DOCUMENTS

2007/0073356 A1     3/2007   Rooney
2014/0163640 A1     6/2014   Edgerton
(Continued)

FOREIGN PATENT DOCUMENTS

WO          2014164414 A1    10/2014

OTHER PUBLICATIONS

Maguire, Greg, "Exosomes: smart nanospheres for drug delivery naturally produced by stem cells", 2016, Fabrication and Self-Assembly of Nanobiomaterials, Chapter 7, pp. 179-209 (Year: 2016).*

(Continued)

*Primary Examiner* — Christine H Matthews
(74) *Attorney, Agent, or Firm* — Fish IP Law, LLP

(57)          ABSTRACT

Systems, methods, and devices are disclosed for administering a therapeutic agent to a patient and improving therapeutic effects of such agents on a patient. A stimulation is applied to a portion of a patient's spine, and the therapeutic agent is administered to the patient intrathecally and proximal to the portion of the patient's spine. In some embodiments, a second stimulation is applied to the patient at a second portion of the patient's spine and concurrently with administering the therapeutic agent. Concerted stimulation of the patient's spine administering a therapeutic agent synergistically improves treatment outcome.

14 Claims, 1 Drawing Sheet

100

110
A first stimulation is applied to a first portion of a patient's spinal cord.

The first stimulation is applied to the epidural space of the patient's spine. — 112

Applying the first stimulation increases a flow of blood in the patient's spinal canal. — 114

The first stimulation is at least one of electrical, thermal, tactile, magnetic, acoustic, or photonic. — 116

The first portion of the patient's spinal cord is one of the patient's vertebra. — 118

120
A therapeutic agent is administered to the patient after the step of applying the first stimulation.

The therapeutic agent is at least one of an exosome or a stem cell. — 122

The therapeutic agent is administered intravenously or intrathecally. — 124

A second stimulation different than the first stimulation is applied to a second portion of the patient's spinal cord and at least partially overlaps with administering the therapeutic agent. — 126

130
A treatment outcome for the patient is improved.

The treatment outcome is related to a neurological condition, such as a neurodegenerative disease or neurotrauma. — 132

(51) Int. Cl.
  *A61N 1/36*          (2006.01)
  *A61N 2/02*          (2006.01)
  *A61N 5/06*          (2006.01)
  *A61N 7/00*          (2006.01)

(56) References Cited

U.S. PATENT DOCUMENTS

| | | |
|---|---|---|
| 2016/0045740 A1 | 2/2016 | Rezai |
| 2016/0235977 A1 | 8/2016 | Lu |
| 2017/0246452 A1 | 8/2017 | Liu |

OTHER PUBLICATIONS

Aslan et al., "Epidural Spinal Cord Stimulation of Lumbosacral Networks Modulates Arterial Blood Pressure in Individuals With Spinal Cord Injury-Induced Cardiovascular Deficits," Frontiers in Physiology, vol. 9, Article 565, May 2018, 11 pages.

Kapural et al., "Novel 10-kHz High-frequency Therapy (HF10 Therapy) Is Superior to Traditional Low-frequency Spinal Cord Stimulation for the Treatment of Chronic Back and Leg Pain," the American Society of Anesthesiologists, Inc. Wolters Kluwer Health, Inc., vol. 123, No. 4, Oct. 2015, pp. 851-860.

"Nevro—1.5 Tesla and 3 Tesla Magnetic Resonance Imaging (MRI) Guidelines for the Senza II™ Implantable Pulse Generator (IPG2000)", Nevro Corp., Jan. 2018, 22 pages.

"Nevro—1.5 Tesla and 3 Tesla Magnetic Resonance Imaging (MRI) Guidelines for the Senza System (IPG1000 and PG1500)", Nevro Corp., Jan. 2018, 22 pages.

"Nevro—Patient-Manual (11052)", Nevro Corp., Jan. 2018, 49 pages.

West et al, "Association of Epidural Stimulation With Cardiovascular Function in an Individual With Spinal Cord Injury", JAMA Neurology, vol. 75, No. 5, May 2018, pp. 630-632.

International Search Report dated Aug. 13, 2020, for related PCT application No. PCT/US2020/031454. 5 pages.

\* cited by examiner

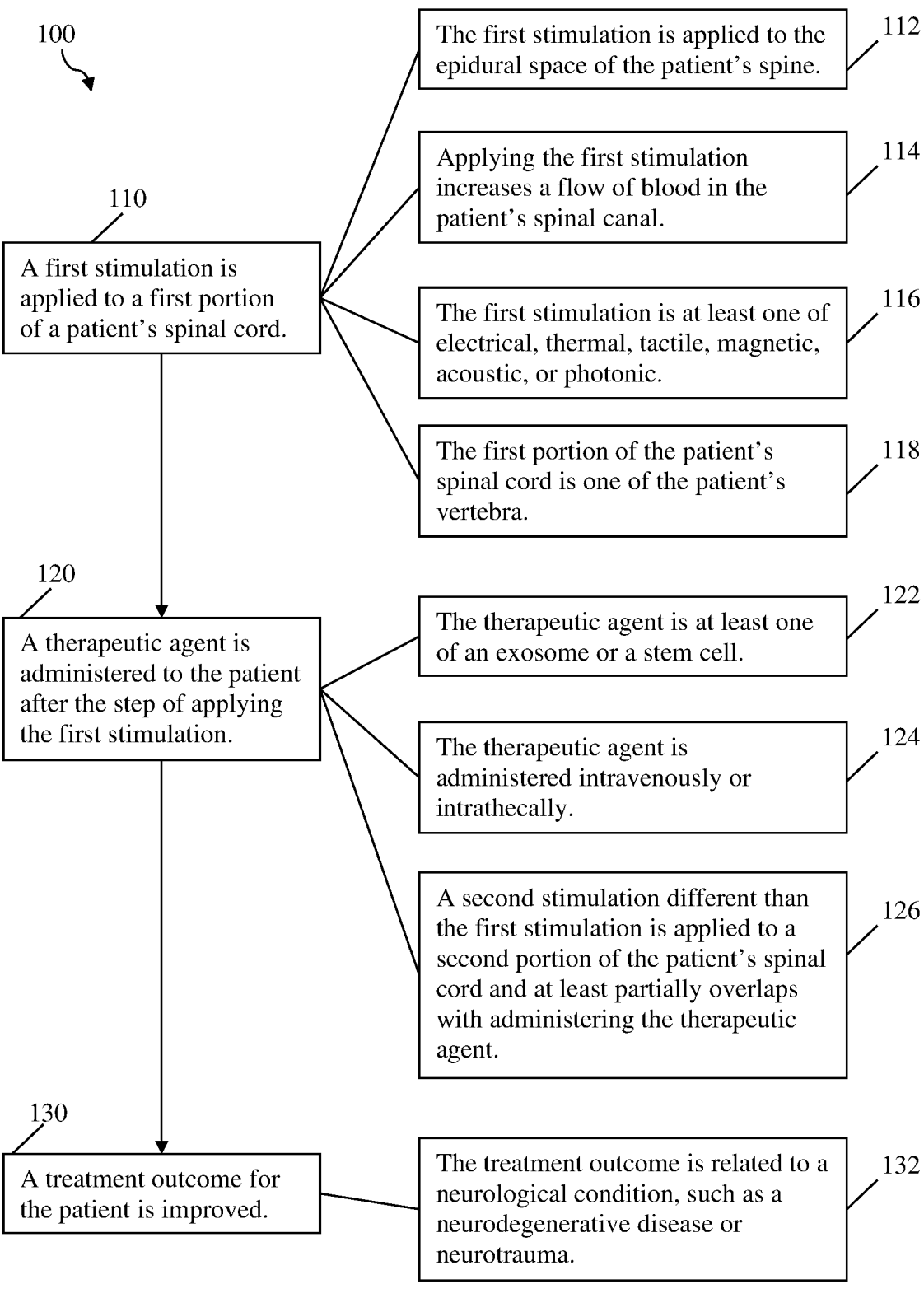

SYSTEMS AND METHODS FOR IMPROVING DELIVERY OF THERAPEUTICS TO THE SPINAL CORD

This application claims priority to U.S. provisional application No. 62/843,663, filed May 6, 2019, the disclosure of which is incorporated herein by reference.

FIELD OF THE INVENTION

The field of the invention is methods, systems, kits, and devices related to improving delivery of therapeutics to patients.

BACKGROUND

The background description includes information that may be useful in understanding the present invention. It is not an admission that any of the information provided herein is prior art or relevant to the presently claimed invention, or that any publication specifically or implicitly referenced is prior art.

When developing possible therapies for neurological conditions, diseases, or disorders, a key obstacle is how the therapy will be delivered or administered to the therapeutic region of interest in the brain. While surgical administration to the brain is possible, in many cases it is unfavorable as it requires access through sensitive intermediate brain tissue and otherwise poses risk of contaminating brain matter, for example with prions. Methods of indirect administration are also known, such as administering therapeutic agents to the blood stream or applying energy pulses to portions of the brain or central nervous system. For example, Kapural et al, Novel 10 kHz High-Frequency Therapy (HF10 Therapy), Anesthesiology 2015 ("Kapural") teaches using electrical pulses via spinal epidural electrodes at vertebral levels to reduce sensation of chronic pain, including pulses of short duration (e.g., 30 μs), high frequency (e.g., 10 kHz), and low amplitude (e.g., 1 mA-5 mA). Likewise, WO2014/164414 to Rezai teaches using electrodes to stimulate the spinal sections and spinal nervous tissue of patients, including in some cases delivering drugs or stem cells to those spinal sections, in order to treat post-traumatic stress related disorders. However, such teachings affect spinal tissue primarily and do not relate to applying therapeutics to brain tissue. Further, while West et al, Association of Epidural Stimulation with Cardiovascular Function, JAMA Neurology 2018 teaches stimulation of lumbosacral spinal cord can be used in patients with motor-complete cervical spinal cord injury to increase systolic blood pressure, middle cerebral artery blood velocity, raw steady state blood pressure, and posterior cerebral artery velocity. However, there appears to be a failure in the art to appreciate the synergistic benefits of applying spinal cord stimulation in concert with intravenous administration of brain tissue targeted therapeutics.

All publications identified herein are incorporated by reference to the same extent as if each individual publication or patent application were specifically and individually indicated to be incorporated by reference. Where a definition or use of a term in an incorporated reference is inconsistent or contrary to the definition of that term provided herein, the definition of that term provided herein applies and the definition of that term in the reference does not apply.

Thus, there remains a need for systems, methods, and devices for synergistically improving treatment outcome through intrathecal administration of therapeutics in concert with spinal cord stimulation.

SUMMARY OF THE INVENTION

The inventive subject matter provides apparatus, systems, and methods for improving a treatment outcome from administering a therapeutic agent to a patient. A stimulation is applied to a portion of the patient's spine, for example at one or more of the vertebrae (e.g., cervical, thoracic, lumbar, sacral, coccygeal, cauda equina, or various portions or combinations thereof), at one or more of the spinal cord segments (e.g., cervical, cervical enlargement, thoracic, lumbar, lumbosacral enlargement, sacral, coccygeal, conus medullaris, or various portions or combinations thereof), at one or more of the spinal nerve roots (e.g., cervical, thoracic, lumbar, sacral, coccygeal, or various portions or combinations thereof), or various portions or combinations thereof. Preferably, the stimulation is applied at least in or around the epidural space of the patient's spine. In preferred embodiments, application of the stimulation to the portion or portions of the patient's spine increases a flow of blood in the patient's spinal canal.

The inventive subject matter also contemplates devices, systems, and methods for administering a therapeutic agent to a patient. A stimulation is applied to a portion of the patient's spinal cord, and the therapeutic agent is administered to the patient after the step of applying the stimulation. The therapeutic agent is preferably at least one of an exosome or a stem cell, and in preferred embodiments is administered intrathecally. The therapeutic agent treats a neurological condition, for example a neurodegenerative condition or a condition related to neurotrauma. Applying the stimulation preferably increases a flow of blood in the patient's spine, for example in the spinal canal.

Uses of the inventive subject matter to treat a neurodegenerative disease or to administer an exosome or a stem cell to a patient are also contemplated.

BRIEF DESCRIPTION OF THE DRAWINGS

FIG. 1 depicts a method of the inventive subject matter.

DETAILED DESCRIPTION

The inventive subject matter provides apparatus, systems, and methods for improving a treatment outcome from administering a therapeutic agent to a patient. A stimulation is applied to a portion of the patient's spine, for example at one or more of the vertebrae (e.g., cervical, thoracic, lumbar, sacral, coccygeal, cauda equina, or various portions or combinations thereof), at one or more of the spinal cord segments (e.g., cervical, cervical enlargement, thoracic, lumbar, lumbosacral enlargement, sacral, coccygeal, conus medullaris, or various portions or combinations thereof), at one or more of the spinal nerve roots (e.g., cervical, thoracic, lumbar, sacral, coccygeal, or various portions or combinations thereof), or various portions or combinations thereof. Preferably, the stimulation is applied at least in or around the epidural space of the patient's spine. In preferred embodiments, application of the stimulation to the portion or portions of the patient's spine increases a flow of blood in the patient's spinal canal, preferably resulting in increased uptake of a therapeutic agent in that region.

The therapeutic agent is administered to the patient preferably after the step of applying the stimulation, but administering the therapeutic agent first or concurrently are also contemplated, alternatively or in combination. The therapeutic agent is generally at least one of an exosome or a stem cell, though therapeutic pharmaceuticals, therapeutic molecules, or therapeutic biologics are further contemplated. Typically, the therapeutic agent is selected to treat a neurological condition, such as a neurodegenerative disease or a condition related to neurotrauma. In some embodiments, the therapeutic agent is administered intravenously, preferably intrathecally and proximal to one or more of the points of stimulation.

The stimulation is typically at least one of electrical (e.g., AC, DC, 1 µA, 10 µA, 100 µA, 1 mA, 10 mA, 100 mA, 1 A, 1V, 10V, 100V, 500V), thermal (e.g., heat, cold), tactile (e.g., pressure, vibration), electromagnetic (e.g., applied magnetic field (e.g., MRI, fMRI), radio waves, microwaves, ionizing radiation), acoustic (e.g., infrasound, audible, ultrasound), or photonic (e.g., laser, ultraviolet, infrared, visible light), though combinations of such sources of stimulation are also contemplated. Likewise, the stimulation can be applied in pulses, for example no more than 0.1 Hz, 1 Hz, 2 Hz, 5 Hz, 10 Hz, 100 Hz, 1 MHz, 1 GHz, or no more than 1 THz, or durations of 1 µs 10 µs, 100 µs, 1 ms, 10 ms, 100 ms, 1 s, 10 s, 1 min, 10 min, or 30 min. For preferred embodiments employing pulsed stimulation, the frequency is associated with the patient's heart beat frequency (HB=heart beat per minute), for example 0.1 HB, 0.5 HB, 1 HB, 2 HB, 5 HB, 10 HB, 100 HB, 1 MHB, 1 GHB, or no more than 1 THB. The stimulation can also be applied in a continuous fashion (e.g., heat compress at 110° F., 115° F., 120° F., 125° F., 130° F., 135° F., 140° F., etc), and can include a plurality of stimulations applied in continuous fashion (e.g., heat compress at 120° F. with infrared light, etc), pulsed fashion (e.g., vibration at 100 Hz with electrical pulse at 1 Hz, etc), or combinations thereof (e.g., heat compress at 120° F. for 10 min with electrical pulse at 1 Hz for 5 s, etc).

For example, in some embodiments a second stimulation is applied to a portion of the patient's spine at least partially continuous with the first stimulation. The second stimulation is typically applied to a second portion of the spine different than the first stimulation, though at least one of the first or second stimulations is preferably directed at the epidural space of the patient's spine. For example, in some embodiments the first stimulation is applied to the patient's skin, while the second stimulation is applied subcutaneously. The second stimulation is generally different than the first stimulation, and is applied at a different frequency or duration. It is contemplated that the first and second stimulations are each selected from the group of electrical, thermal, tactile, magnetic, acoustic, or photonic, and either directly (e.g., in direct contact or communication) or indirectly (e.g., stimulate the patient's skin, neighboring tissue, or pass through tissue, etc.) affect the targeted portions of the spine. The therapeutic agent is typically administered after the first stimulation, and in some embodiments at least partially concurrent with the second stimulation.

The treatment outcome is associated with the patient's central nervous system, for example a neurological condition of the patient, preferably a neurodegenerative disease or a neurotrauma. Surprisingly, methods of the inventive subject matter including stimulation of the patient's spine in conjunction with administering therapeutic agents to the patient improves the patient's neurological condition by at least 5%, 10%, 15%, 20%, 25%, 30%, 35%, 50%, 100%, or more than 150% compared to administering the stimulation or therapeutic agent to the patient in isolation. Moreover, the effect of stimulating the patient's spine in combination with administering a therapeutic agent to the patient has a synergistic improvement in therapy outcome compared to the sum of the outcome achieved by either spinal stimulation or administration of therapeutic agent in isolation. For example, where spinal stimulation achieves a 10% improvement in the patient's neurological condition, and administration of therapeutic agent achieves a 20% improvement in the patient's neurological condition, the methods of the inventive subject matter of combining spinal stimulation with administration of therapeutic agents (e.g., exosome, stem cell, etc) surprisingly improves the patient's neurological condition by more than 30%, for example 40%, 50%, 60%, 70%, 80%, 90%, or more than 100% improvement.

It should be appreciated that while the inventive subject matter applies stimulation to portions of the patient's spine or neighboring tissue, the primary therapeutic effect of the inventive subject matter is to improve delivery of a therapeutic agent to the patient's spine or nervous tissue. Indeed, stimulating the patient's spine and administering a therapeutic agent to the patient in a concerted manner causes a synergistic improvement in the treatment of a neurological condition or trauma, and otherwise synergistically improves patient outcome.

The inventive subject matter also contemplates devices, systems, and methods for administering a therapeutic agent to a patient. A stimulation is applied to a portion of the patient's spinal cord, and the therapeutic agent is administered to the patient after the step of applying the stimulation. The therapeutic agent is preferably at least one of an exosome or a stem cell, and in preferred embodiments is administered intrathecally. The therapeutic agent treats a neurological condition, for example a neurodegenerative condition or a condition related to neurotrauma. Applying the stimulation preferably increases a flow of blood in the patient's spine, for example in the spinal canal.

Uses of the inventive subject matter to treat a neurodegenerative disease or to administer an exosome or a stem cell to a patient are also contemplated.

Methods, systems, and devices are further contemplated for administering a therapeutic agent to a patient, including stimulating an epidural space of the patient's spine to increase blood flow in the patient's spinal canal and intrathecally administering the therapeutic agent to the patient, either simultaneously or in sequence, with the therapeutic agent an exosome, a stem cell, a plurality of different exosomes, a plurality of different stem cells, or some combination thereof. In preferred embodiments, the therapeutic agent is administered after, and temporally proximal, to the step of stimulating the epidural space, for example within 0.1 s, 1 s, 2 s, 3 s, 4 s, 5 s, 10 s, or 30 s of stimulating the epidural space, and in some embodiments at least partially overlaps with stimulation of the epidural space.

FIG. 1 depicts method 100 of the inventive subject matter, including required steps 110, 120, and 130. Optional steps 112, 114, 116, and 118 can be performed with step 110, optional steps 122, 124, and 126 can be performed with step 120, and optional step 132 can be performed with step 130, or combinations thereof.

The following description includes information that may be useful in understanding the present invention. It is not an admission that any of the information provided herein is prior art, necessary, or relevant to the presently claimed invention, or that any publication specifically or implicitly referenced is prior art.

As used in the description herein and throughout the claims that follow, the meaning of "a," "an," and "the" includes plural reference unless the context clearly dictates otherwise. Also, as used in the description herein, the meaning of "in" includes "in" and "on" unless the context clearly dictates otherwise.

As used herein, and unless the context dictates otherwise, the term "coupled to" is intended to include both direct coupling (in which two elements that are coupled to each other contact each other) and indirect coupling (in which at least one additional element is located between the two elements). Therefore, the terms "coupled to" and "coupled with" are used synonymously.

Unless the context dictates the contrary, all ranges set forth herein should be interpreted as being inclusive of their endpoints, and open-ended ranges should be interpreted to include commercially practical values. Similarly, all lists of values should be considered as inclusive of intermediate values unless the context indicates the contrary.

The recitation of ranges of values herein is merely intended to serve as a shorthand method of referring individually to each separate value falling within the range. Unless otherwise indicated herein, each individual value is incorporated into the specification as if it were individually recited herein. All methods described herein can be performed in any suitable order unless otherwise indicated herein or otherwise clearly contradicted by context. The use of any and all examples, or exemplary language (e.g. "such as") provided with respect to certain embodiments herein is intended merely to better illuminate the invention and does not pose a limitation on the scope of the invention otherwise claimed. No language in the specification should be construed as indicating any non-claimed element essential to the practice of the invention.

Groupings of alternative elements or embodiments of the invention disclosed herein are not to be construed as limitations. Each group member can be referred to and claimed individually or in any combination with other members of the group or other elements found herein. One or more members of a group can be included in, or deleted from, a group for reasons of convenience and/or patentability. When any such inclusion or deletion occurs, the specification is herein deemed to contain the group as modified thus fulfilling the written description of all Markush groups used in the appended claims.

The following discussion provides many example embodiments of the inventive subject matter. Although each embodiment represents a single combination of inventive elements, the inventive subject matter is considered to include all possible combinations of the disclosed elements. Thus if one embodiment comprises elements A, B, and C, and a second embodiment comprises elements B and D, then the inventive subject matter is also considered to include other remaining combinations of A, B, C, or D, even if not explicitly disclosed.

It should be apparent to those skilled in the art that many more modifications besides those already described are possible without departing from the inventive concepts herein. The inventive subject matter, therefore, is not to be restricted except in the scope of the appended claims. Moreover, in interpreting both the specification and the claims, all terms should be interpreted in the broadest possible manner consistent with the context. In particular, the terms "comprises" and "comprising" should be interpreted as referring to elements, components, or steps in a non-exclusive manner, indicating that the referenced elements, components, or steps may be present, or utilized, or combined with other elements, components, or steps that are not expressly referenced. Where the specification claims refers to at least one of something selected from the group consisting of A, B, C . . . and N, the text should be interpreted as requiring only one element from the group, not A plus N, or B plus N, etc.

What is claimed is:

1. A method of improving a treatment outcome from administering a therapeutic agent to a patient, comprising:
    applying a first stimulation to an epidural space of the patient's spinal cord;
    applying a second stimulation to a portion of the patient's spinal cord after the first stimulation; and
    administering the therapeutic agent to the patient at a site proximal to the portion of the patient's spinal cord after the step of applying the first stimulation and partially concurrent with applying the second stimulation;
    wherein the first stimulation and the second stimulation are each at least one of thermal, tactile, electromagnetic, acoustic, or photonic; and
    wherein the epidural space and the portion of the patient's spinal cord are located at different portions of the patient's spinal cord.

2. The method of claim 1, wherein the therapeutic agent is at least one of an exosome or a stem cell.

3. The method of claim 1, wherein the therapeutic agent is administered either intravenously or intrathecally.

4. The method of claim 1, wherein the first stimulation is applied to the epidural space of the patient's spinal cord via the patient's skin.

5. The method of claim 1, further comprising the step of at least partially increasing a flow of blood in the patient's spinal canal by way of applying the first stimulation.

6. The method of claim 1, wherein the second stimulation is directed at the epidural space.

7. The method of claim 1, wherein the therapeutic agent is administered intrathecally.

8. The method of claim 1, wherein the therapeutic agent is an exosome.

9. The method of claim 8, wherein the therapeutic agent is administered intrathecally.

10. The method of claim 1, wherein the first stimulation and the second stimulation are different types of stimulation.

11. The method of claim 1, wherein the therapeutic agent is administered within 30 seconds of applying the first stimulation to the epidural space.

12. The method of claim 11, wherein the therapeutic agent is administered within 5 seconds from applying the first stimulation to the epidural space.

13. The method of claim 1, wherein the therapeutic agent is selected to treat a neurodegenerative disease or condition related to neurotrauma.

14. The method of claim 1, wherein the first stimulation and the second stimulation are each at least one of thermal, electromagnetic, acoustic, or photonic.

* * * * *